United States Patent
Paspaliaris et al.

(10) Patent No.: US 9,752,138 B2
(45) Date of Patent: Sep. 5, 2017

(54) METHODS AND APPARATUSES FOR ISOLATING AND PREPARING STEM CELLS

(71) Applicant: AdiStem, Ltd., Wanchai (HK)

(72) Inventors: Bill Paspaliaris, Victoria (AU); James Andrew Farrant Thornton, Makati (PH)

(73) Assignee: ADISTEM LTD., Wanchai (HK)

( * ) Notice: Subject to any disclaimer, the term of this patent is extended or adjusted under 35 U.S.C. 154(b) by 23 days.

(21) Appl. No.: 14/045,828

(22) Filed: Oct. 4, 2013

(65) Prior Publication Data
US 2014/0093482 A1    Apr. 3, 2014

Related U.S. Application Data

(62) Division of application No. 13/266,834, filed as application No. PCT/CN2010/072041 on Apr. 22, 2010.

(30) Foreign Application Priority Data

Apr. 30, 2009   (AU) ................................ 2009100401

(51) Int. Cl.
| | | |
|---|---|---|
| *C12N 5/00* | (2006.01) | |
| *C12N 13/00* | (2006.01) | |
| *A61K 35/12* | (2015.01) | |
| *C12N 5/0775* | (2010.01) | |

(52) U.S. Cl.
CPC .............. *C12N 13/00* (2013.01); *A61K 35/12* (2013.01); *C12N 5/0667* (2013.01); *C12N 2500/36* (2013.01); *C12N 2501/135* (2013.01); *C12N 2501/70* (2013.01)

(58) Field of Classification Search
CPC ....................................................... C12N 13/00
USPC .......................................................... 435/325
See application file for complete search history.

(56) References Cited

U.S. PATENT DOCUMENTS

2006/0184214 A1 * 8/2006 McDaniel ....................... 607/89

OTHER PUBLICATIONS

Mvula et al. (e-published Jan. 27, 2009, Lasers Med. Sci., vol. 25, pp. 33-39).*
Kakudo et al. (2008, Plast. Reconstr. Surg., vol. 122, pp. 1352-1360).*
Carey et al. (1983, Ann. Rev. Physiol., vol. 45, pp. 651-677).*

* cited by examiner

*Primary Examiner* — Thaian N Ton
*Assistant Examiner* — David A Montanari
(74) *Attorney, Agent, or Firm* — King & Schickli, PLLC

(57) ABSTRACT

The present invention relates to a method of preparing a population of stem cells for autologous implantation to a subject. The cells are activated by irradiating the cells with one or more wavelengths of yellow and red and/or green light. In particular, the cells are irradiated with 575-595 nm (5-20 mW), and 630-635 nm or 660-670 nm (10-100 mW) and/or 510-540 nm (10-60 mW) of monochromatic light for 30-60 mins. Preferably the stem cells are adipose-derived stem cells. Also the invention relates to therapeutic applications of the activated stem cells.

10 Claims, 10 Drawing Sheets

Method for Harvesting*

Figure 1:
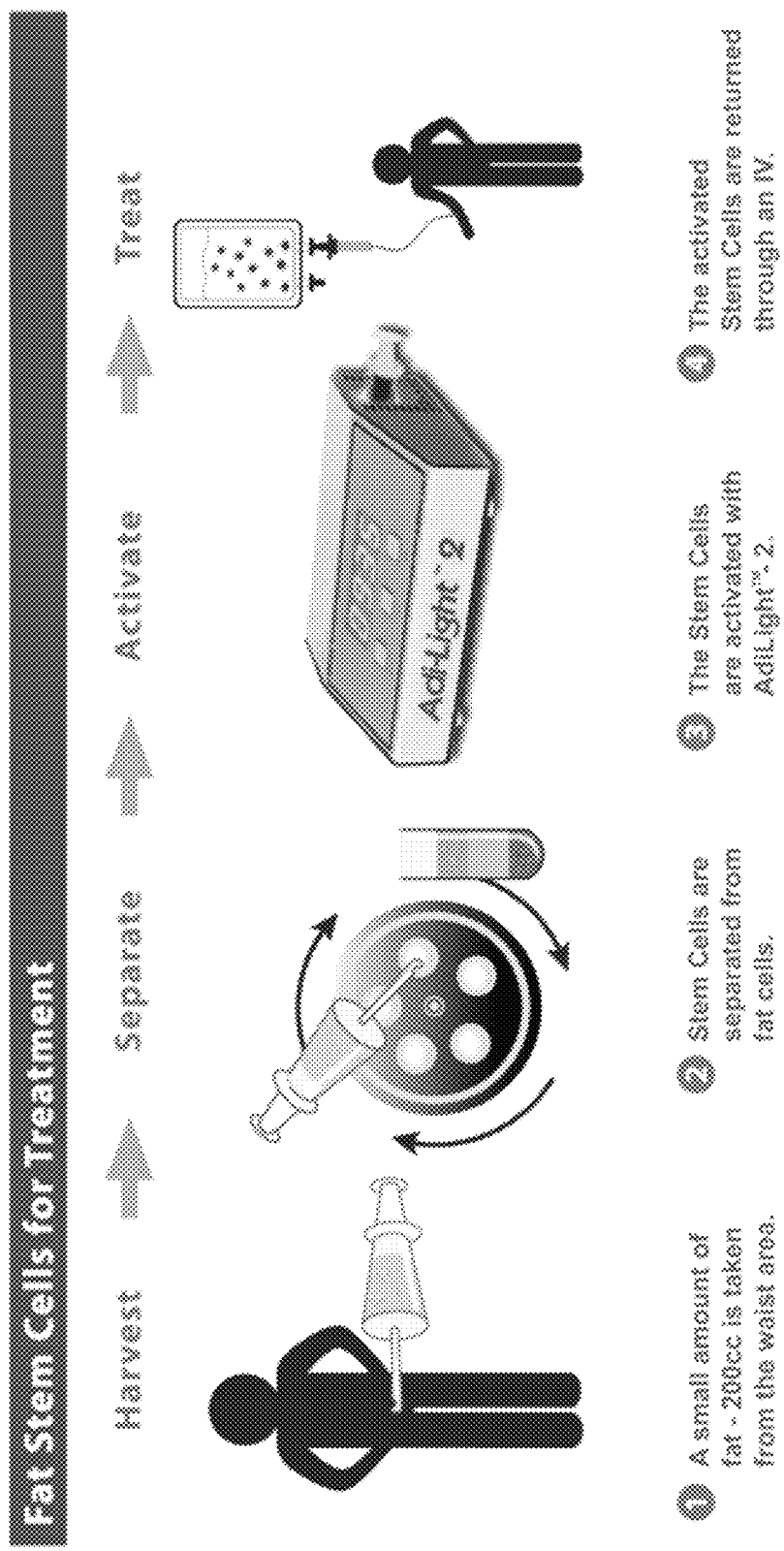

- Total cells:
  - ▨ Standard method: 10,053 viable cells per microlitre (10 million per cc fat)
  - ▨ Adistem: 12,003 viable cells per microlitre (12 million per cc fat)

- CD 29
  - ▨ Standard method: 78.23%
  - ▨ Adistem: 98.56%

- CD 90
  - ▨ Standard method: 86.30%
  - ▨ Adistem: 89.84%

- CD29 and CD90 are mesenchyme cell markers.

\* Independent analysis was done by EU accredited cGMP laboratory.

Figure 2

Light activation

| Treatment | Adipose MSC Number of cells (MTT) |
|---|---|
| Control | 0.595 ± 0.056 |
| Irradiated (LLL) | 0.675 ± 0.050* |
| Irradiated (LED-infrared) | 0.676 ± 0.049* |
| Irradiated (LED-yellow) | 0.711 ± 0.053* |
| Irradiated (LED-red) | 0.741 ± 0.059* |
| Irradiated (LED-green) | 0.775 ± 0.043* |
| Adistem Laser (Gre, Yel, Red) | 0.900 ± 0.053** |

Figure 4

Diabetes Parameters

DIABETES PARAMETERS

Fasting Blood Sugar (mmol/L)

| Baseline | 2 weeks po | 12 weeks po | 24 weeks po | 36 weeks po | 48 weeks | p value | n |
|---|---|---|---|---|---|---|---|
| 9.64+3.87 | 7.01+1.64* | 7.71+2.29* | 8.39+2.82 | 7.04+2.20* | 7.00+2.04* | <0.01 | 31 |

Glycosalated Haemoglobin (HbA1c %)

| Baseline | 12 weeks po | 24 weeks po | 36 weeks po | 48 weeks | p value | n |
|---|---|---|---|---|---|---|
| 9.11+2.06 | 7.73+1.19** | 8.03+1.82** | 7.48+1.38** | 7.88+1.84** | <0.001 | 31 |

C-Peptide (ng/ml)

| Baseline | 12 weeks po | 24 weeks po | 36 weeks po | 48 weeks | p value | n |
|---|---|---|---|---|---|---|
| 2.75+1.01 | 2.27+1.44* | 2.85+1.34 | 2.31+1.14* | 2.81+2.9 | <0.05 | 31 |

UROLOGICAL PARAMETERS

BUN

*No statistically significant change over 12 months*

Creatinine

*No statistically significant change over 12 months*

HEPATIC PARAMETERS

Total Cholesterol

*No statistically significant change over 12 months*

Triglycerides

| Baseline | 12 weeks po | 24 weeks po | 36 weeks po | p value | n |
|---|---|---|---|---|---|
| 2.31+1.53 | 1.91+1.63** | NS | NS | **0.03 | 31 |

SGOT

*No statistically significant change over 12 months*

SGPT

*No statistically significant change over 12 months*

Figure 8

METHODS AND APPARATUSES FOR ISOLATING AND PREPARING STEM CELLS

This utility patent application is a division of prior U.S. patent application Ser. No. 13/266,834 filed on Jan. 10, 2012, which was the national stage of International Application No. PCT/CN2010/072041 filed on Apr. 22, 2010, which in turn claims priority from Australian Patent Application No. 2009100401 filed on Apr. 30, 2009, the entirety of the disclosures of which are incorporated herein by reference

TECHNICAL FIELD

The present application provides methods for preparing stem cells for use in autologous implantation. The application also provides means of activating stem cells and apparatuses that can be used in the methods of the invention.

Regenerative medicine harnesses the body's regenerative mechanisms in a clinically targeted manner, using them in ways that are not part of the normal healing mechanism or by artificially amplifying normal mechanisms.

An example of this process is found in bone marrow transplantation where hematopoietic stem and progenitor cells are harvested from a donor and placed into a recipient in whom the normal hematopoietic regenerative mechanisms have been ablated or substantially depleted or impaired, thereby replacing or regenerating the blood-forming capacity of the recipient. In recent clinical and pre-clinical studies this approach has been extended to the non-hematopoietic stem cell component of bone marrow with studies regenerating (or attempting to regenerate) tissues including bone, heart, and liver. Such work has been based on the detection of the presence of non-hematopoietic stem cells and endothelial precursor cells in bone marrow.

Such studies used bone marrow transplant recipient animals in which donor and host cells could be distinguished by genetic markers to show that some fraction of new blood vessel development in the recipients was derived from the donor marrow cells. While this work demonstrates that marrow contains such cells, it has generally been extended to mean that marrow is therefore the only tissue that contains relevant numbers of such cells, to the extent that when an investigator detects endothelial precursor cells (EPCs) or marrow stem cells (MSCs) in the circulation it is automatically assumed that these cells are necessarily marrow-derived. Thus, the concept that cell populations from other tissues might represent an alternative, or perhaps superior, source of therapeutically relevant cell populations is not addressed.

It has been demonstrated that adipose tissue contains a population multipotent stem cells and it has previously shown that this tissue can be used as a source of endothelial cells, though such studies did not examine and do not speak in any way to endothelial precursor cells.

Stem cells from embryos or embryonic stem cells (ESCs) are known to become many, if not all, of the cell and tissue types of the body. These early foetal cells not only contain all the genetic information of the individual but also contain the nascent capacity to become any of the cells and tissues of the body. Ongoing research suggests that stem cells have tremendous scientific and clinical potential.

However, ESCs have theoretic limitations to their use. If used clinically they would necessarily be derived from another individual, i.e. an embryo. When stem cells or tissues derived from them are transplanted into another person, toxic immune suppressing drugs may be needed by the cell recipient to prevent rejection. In addition, another individual's cells can carry viruses or other rare but significant diseases that can be transmitted to the recipient. Also, ESC-like cells (eg. teratomas) are known to form tumors.

Recently, non-embryonic or adult stem cells have been identified and represent an alternative to the clinical use of ESCs. These cells reside in many, if not all, tissues, presumably waiting to respond to trauma or other destructive disease processes so that they can heal the injured tissue. Emerging scientific evidence indicates that each individual carries a pool of stem cells that may share with ESCs the ability to become many if not all types of cells and tissues.

Adult stem cell populations have been shown to be present in skin, muscle, marrow, liver, brain, and adipose tissue. To date the proposed application of such cells in tissue engineering involve increasing cell number, purity, and maturity, by processes of cell purification and cell culture. These steps are necessary to compensate for the rarity of stem cells in most tissues. For example, mesenchymal stem cell frequency in bone marrow is estimated at between 1 in 100,000 and 1 in 1,000,000 nucleated cells. Similarly, extraction of stem cells from skin involves a complicated series of cell culture steps over several weeks. Use of skeletal muscle-derived stem cells in clinical trials of heart disease employs a two to three week culture phase, in which cell number is increased to clinically relevant numbers and cell differentiation into muscle is promoted.

These expansion and differentiation steps may provide increased cell number, purity, and maturity, but they do so at a cost. This cost can include one or more of: loss of cell function due to cell aging, loss of potentially useful non-stem cell populations, delays in potential application of cells to patients, increased monetary cost, and increased risk of contamination of cells with environmental microorganisms during culture. While human data is now becoming available with marrow-derived cells that have not been manipulated but rather used as essentially whole marrow, the clinical benefit derived has been suboptimal; an outcome almost certainly related to the limited cell dose and purity available from marrow.

From the above it can be seen that there remains the need for methods for preparing stem cell populations for regenerative medicine purposes, in which a population of active cells with increased yield, consistency and/or purity can be prepared rapidly and reliably, in a cost effective manner.

DESCRIPTION OF THE INVENTION

While it is to be understood that the aspects of the invention described herein can be generally applied to any population of stem cells, this section of the description discusses adipose-derived stem cells (ADSC) as an example of such stem cells, The present invention is directed to methods for preparing adipose-derived stem cells (ADSC) from adipose tissue, and methods and systems for activating ADSC derived from adipose tissue that are placed directly into a recipient to promote, engender, or support a therapeutic, structural, or cosmetic benefit.

In one embodiment, adipose tissue processing occurs in a system that maintains a closed, sterile fluid/tissue pathway. This is achieved by use of a pre-assembled, closed sterile container and tubing, allowing for transfer of tissue and fluid elements within a closed pathway. A series of processing reagents (e.g., saline, enzymes, etc.) can be inserted into the container in which the operators manually manage the process.

Preferably the entire procedure from tissue extraction through processing and placement into the recipient would all be performed in the same premises, or more so even within the same room of the patient undergoing the procedure.

For one particular aspect of the invention, raw adipose tissue is processed to remove lipid-containing adipocytes and connective tissue thereby obtaining a composition of cells suitable for placement within the body of a recipient. The cells are then activated with stimulators of cell growth and/or differentiation, optionally derived from growth factors from the patients own platelets, and/or irradiated with monochromatic photomodulation. The activated cells, with any of the above mentioned additives or irradiation, are placed into the person from whom they were obtained in the context of an autologous single operative procedure with the intention of deriving a therapeutic, structural, or cosmetic benefit to the recipient.

A method of treating a patient includes steps of:

a) removing adipose tissue from a patient using liposuction or lipoplasty in which the adipose tissue has a concentration of stem cells;

b) processing the adipose tissue to obtain a higher concentration of stem cells than before processing, for example by the use of soy lecithin;

c) activating the final composition of stem cells with stimulators of stem cells growth and differentiation, for example by the use of use of autologous platelet-derived growth factors with laser light irradiation;

d) administering the activated stem cell composition to a patient.

In another embodiment, a method of treating a patient includes:

a) removing adipose tissue from a patient using liposuction or lipoplasty in which the adipose tissue has a concentration of stem cells;

b) processing the adipose tissue to obtain a higher concentration of stem cells than before processing, for example by the use of soy lecithin;

c) activating the final composition of stem cells with stimulators of stem cells growth and differentiation, for example by the use of use of autologous platelet-derived growth factors with laser light irradiation;

d) mixing the adipose tissue having the concentrated stem cells with another portion of adipose tissue;

e) administering the adipose tissue with the increased concentration of stem cells to a patient.

By administering the activated cells to a patient, one can treat numerous diseases, including, and not limited to, bone-related disorders; adipose related disorders or diseases; liver related diseases; myocardial infarctions; renal diseases; retinal diseases; wound healing (e.g., from surgery or diabetic ulcers); skeletal muscle disorders; cartilage and joint repair; lung injuries; diabetes; intestinal disorders; and nervous system disorders, diseases, or injuries.

The activated stem cells may also be administered to a patient for cosmetic purposes, such as by enhancing physical features, including reducing wrinkles, enhancing organ mass, and the like.

Hence we disclose a lipid dissolving agent (composed of soy lecithin) added at the end of enzymic digestion of adipose tissue for the purpose of extracting a composition of cells that has an increase concentration of adipose derived stem cells and a reduced total lipid concentration We also disclose where activation of extracted adipose-derived stem cells is performed with the patients own platelet-derived growth factors We also disclose where activation of extracted adipose-derived stem cells is performed by irradiating them with a combination of various frequencies (preferably green, yellow and red) of monochromatic light (preferably by laser).

We also disclose methods wherein one or more combinations of the above statements are used.

FURTHER DESCRIPTION OF THE INVENTION

Reference will now be made in detail to the presently preferred embodiments of the invention, examples of which are illustrated in the accompanying drawings.

The present invention may be practiced in conjunction with various cell or tissue separation techniques that are conventionally used in the art, and only so much of the commonly practiced process steps are included herein as are necessary to provide an understanding of the present invention.

While the present invention is generally directed to any population of stem cells, a preferred embodiment of the invention is directed to a cell population present in adipose tissue, and systems and methods for administering the cell population into a human or animal patient. The cell population of the adipose tissue may be used as a source of cells for therapeutic and cosmetic applications. Among other things, the cells may be used for regenerative medicine, such as diseases that can be treated with regenerating cells. The cells of the population may be administered to a patient without other adipocytes or connective tissue, or may be administered mixed together with adipose tissue in a concentrated amount, as discussed herein.

It has been discovered that adipose tissue is an especially rich source of stem cells. This finding may be due, at least in part, to the ease of removal of the major non-stem cell component of adipose tissue, the adipocyte. Thus, in both human and animal studies, processed lipoaspirate (PLA) contains stem cells at a frequency of at least 0.1%, and more typically greater than 0.5%. In certain embodiments of the invention, PLA has been obtained which contains between about 2-12% stem cells. In even further embodiments, the PLA is processed to obtain a population of cells where the stem cells constitute between up to 100% of the cells in the population. The amount of stem cells obtained in accordance with the invention herein disclosed is substantially greater than the published frequency of 1 in 100,000 (0.001%) in marrow (Castro-Malaspina, H., W. Ebell, et al. (1984), Prog Clin Biol Res 154: 209-36; Muschler, G. F., H. Nitto, et al. (2001), J Orthop Res 19(1): 117-25). Furthermore, collection of adipose tissue is associated with lower morbidity than collection of a similar volume of marrow (Nishimori, M., Y. Yamada, et al. (2002), Blood 99(6): 1995-2001). In addition, adipose tissue contains endothelial precursor cells, which are capable of providing therapy to patients (see for example Masuda, H., C. Kalka, and T. Asahara (2000), Hum Cell. 13(4): p. 153-60; Kaushal, S., et al., (2001), Nat Med 7(9): p. 1035-40; and Kawamoto, A., et al. (2001) Circulation 103(5): p. 634-7).

The inventors have also determined that it is advantageous to activate stem cells, particularly ADSC, prior to their use for therapeutic and cosmetic applications. As will be described in more detail below, this activation can be performed by irradiation of the cells with specific wavelengths of light, and optionally using a mixture of natural or synthetic growth factors.

A first aspect of the invention provides a method of preparing a population of stem cells for autologous implantation to a subject, comprising activating the stem cells by irradiating the cells with one or more wavelengths of yellow and red and/or green light.

The inventors have determined that it is surprisingly advantageous to irradiate stem cells with one or more specific wavelengths of light, especially monochromatic light, where the light is yellow and red and/or green wavelengths of light, prior to their use in autologous implantation to a subject. While not wishing to be bound to any particular theory, and as described further below, the inventors consider that specific wavelengths of light act as photomodulators which 'activate' the stem cells such that the cells are committed to develop towards certain cell fates. In this way, stem cells can be 'primed' before use such that they can best have a therapeutic and/or cosmetic effect following autologous implantation.

Preferably, one or more lasers can be used as a source of the light. While yellow light can be used in combination with red or green light, it is preferred that all three are used in the method.

By "yellow", "red" and "green" light, we include those wavelengths of light associated with those particular colours. However, preferably in the method of the first aspect of the invention the following wavelengths of monochromatic light and power rating are used: 575-595 nm (5-20 mW) (yellow; this can also be considered to be an "orange" range of wavelengths as well), and 630-635 nm or 660-670 nm (10-100 mW) (red) and/or 510-540 nm (10-60 mW) (green) for 30-60 mins. An embodiment of this aspect of the invention is wherein the cells are irradiated with 595 nm (20 mW), 635 nm (60 mW) and 535 nm (60 mW), of monochromatic light for 30-60 mins.

An embodiment of this aspect of the invention is wherein the method further comprises an initial step of processing a sample of tissue from the subject to obtain the population stem cells. Preferably the stem cells are concentrated to form the said population.

The method of the first aspect of the invention can generally be applied to any population of stem cells.

Stem cells are cells found in most, if not all, multi-cellular organisms. They are characterized by the ability to renew themselves through mitotic cell division and differentiating into a diverse range of specialized cell types. The two broad types of mammalian stem cells are: embryonic stem cells (ESCs) that are isolated from the inner cell mass of blastocysts; and adult stem cells (ASCs) that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin, or intestinal tissues.

Stem cells can now be grown and transformed into specialized cells with characteristics consistent with cells of various tissues such as muscles or nerves through cell culture. Highly plastic adult stem cells from a variety of sources, including umbilical cord blood and bone marrow, are routinely used in medical therapies. Embryonic cell lines and autologous embryonic stem cells generated through therapeutic cloning have also been proposed as promising candidates for future therapies.

Hence by 'stem cells', the present application includes both embryonic stem cells and adult stem cells. However, since the method of the invention relates to the preparation of stem cells for autologous implant, preferably the stem cells are adult stem cells isolated from the patient to be supplied with the prepared stem cells.

By "adult stem cells" we include: adipose-derived stem cells; dermal stem cells; hematopoietic stem cells; mammary stem cells; mesenchymal stem cells; endothelial stem cells; neural stem cells; neural crest stem cells; testicular stem cells.

Adult stem cells been identified in many organs and tissues, including brain, bone marrow, peripheral blood, blood vessels, skeletal muscle, skin, teeth, heart, gut, liver, ovarian epithelium, and testis. They are thought to reside in a specific area of each tissue (called a "stem cell niche"). In many tissues, current evidence suggests that some types of stem cells are pericytes, cells that compose the outermost layer of small blood vessels. Stem cells may remain quiescent (non-dividing) for long periods of time until they are activated by a normal need for more cells to maintain tissues, or by disease or tissue injury.

Methods of isolating and preparing population of stem cells that can be used in the method of the invention will vary according to the stem cell type to be used, and tissue they are to be isolated from. Many examples of methods for preparing stem cells from particular tissues are known and the skilled person would be able to use such methods when preparing a population to be used.

For example, with regard to bone marrow (mesenchymal) stem cells there are many laboratory methods well known in the art that can be used directly or readily adapted so as to provide a population of such stem cells for the invention. Similarly, there are many protocols well known in the art that can be used to isolate peripheral blood stem cells for the invention.

A preferred embodiment of this aspect of the invention is where the stem cells are adipose-derived stem cells (ADSC), and the optional step of processing a sample of tissue from a patient to be treated to obtain the population stem cells uses adipose tissue.

A further embodiment of the first aspect of the invention is wherein the stem cells are exposed to one or more growth factors. The growth factors are Epidermal Growth Factor (EGF); Platelet-Derived Growth Factor (PDGF); Fibroblast Growth Factor (FGFs); Transforming Growth Factors-b (TGFs-b); Erythropoietin (EPO); Insulin-like Growth Factor-I (IGF-I); Insulin-like Growth Factor-II; and/or Tumour Necrosis Factor-a (TNF-a). Preferably the stem cells are exposed to all of the listed growth factors.

A further embodiment of this aspect of the invention is where the growth factors are provided by platelet-rich plasma prepared from the subject. As described further below, the inventors have determined that surprisingly advantageous to expose the preparation of stem cells to growth factors before their use in autologous implantation. While not wishing to be bound to any particular theory, and as described further below, the inventors consider that the growth factors 'activate' the stem cells such that the cells towards certain cell fates. In this way, the stem cells can be 'primed' before use such that they can best have a therapeutic and/or cosmetic effect following autologous implantation. Preferably the growth factors are provided by platelet-rich plasma prepared from the subject. Hence the stem cells are only exposed to autologous growth factors prior to their use in implantation, thus lessening the likelihood of infection and immune reactions.

As described further below, in one embodiment of the invention the method includes where the tissue from the subject is processed to obtain a concentrated population of stem cells. Preferably the step includes exposing said tissue to a lipid dissolving agent, preferably lecithin. In addition collagenase could also be used to disaggregate the tissue so as to prepare the stem cells. Moreover, where the stem cells are ADSC, then the tissue to be used is adipose tissue.

One embodiment of the method of the invention involves adipose tissue as a source of ADSC. Preferably the adipose tissue has been isolated from the patient to be treated by liposuction and/or lipoplasty.

A preferred embodiment of the invention is where the method comprises the following procedure:

i) processing a sample of adipose tissue from the subject to obtain a concentrated population of ADSC, said processing comprising: removing free lipid and single cell components of the tissue by rinsing; disaggregating the tissue using mechanical forces, collagenase and lecithin digestion; separating and concentrating the ADSC using centrifugation;

ii) activating the population of ADSC by irradiating the cells with 575-595 nm (5-20 mW), and 630-635 nm or 660-670 nm (10-100 mW) and/or 510-540 nm (10-60 mW) of monochromatic light for 30-60 mins, and incubating the cells in the presence of platelet-rich plasma prepared from the patient to be treated at 30° C. to 38° C. for 5-120 mins.

Preferably the cells are irradiated with 595 nm (20 mW), 635 nm (60 mW) and 535 nm (60 mW), of monochromatic light for 30-60 mins.

An important advantage of this embodiment of the invention is that sufficient stem cells are prepared from tissue of the subject such that the method does not involve a step of culturing the population of stem cells to increase cell number prior to their use in autologous implantation.

For the avoidance of doubt, the method of the first aspect of the invention relates to the activation of stem cells for autologous implantation to a subject, and may not include a step of administering the activated stem cells to the subject.

By "subject" we preferably mean a human patient to be treated with autologous implantation to alleviate or treat a particular disorder. Examples of disorders which can be treated with the activated stem cells of the invention are provided below.

Also for the avoidance of doubt, in each embodiment of the method of the invention discussed above, it is preferred that the stem cells are ADSC, and where appropriate the tissue is adipose tissue.

A further aspect of the invention provides a population of stem cells for autologous implantation obtained by the method of the first aspect of the invention. Preferably the stem cells are ADSC.

As discussed above, the stem cells prepared according to the method of the invention can be used in methods of treatment. Hence an aspect of the invention provides a method of treating a patient using stem cells for autologous implantation comprising:

(i) isolating tissue from the patient;

(ii) preparing a population of stem cells according to a method of the first aspect of the invention; and (iii) administering the activated population of stem cells to the patient.

Preferably the activated population of stem cells is mixed with a further portion of tissue prior to administration to the patient.

A preferred embodiment of this aspect of the invention is wherein the tissue is adipose tissue, and the stem cells are ADSC.

A preferred embodiment of this aspect of the invention is wherein said patient is treated for therapeutic and/or cosmetic purposes.

A further aspect of the invention provides a population of stem cells prepared according to the method of the first aspect of the invention for use for therapeutic and/or cosmetic purposes. Preferably the stem cells are ADSC.

By "treatment" we include therapeutic and/or cosmetic purposes. Therapeutic purposes includes where the treatment is for bone-related disorders; adipose related disorders or diseases; liver related diseases; myocardial infarctions; renal diseases; retinal diseases; wound healing; skeletal muscle disorders; cartilage and joint repair; lung injuries; diabetes; intestinal disorders; nervous system disorders, diseases, or injuries; diabetes; alopecia. Preferably the diabetes is type II diabetes.

A still further aspect of the invention provides a method of treating a subject comprising activating stem cells in situ in the subject by irradiating the cells with one or more wavelengths of yellow and red and/or green light. Preferably the following wavelengths of monochromatic light and power rating are used: 575-595 nm (5-20 mW) (yellow; this can also be considered to be an "orange" range of wavelengths as well), and 630-635 nm or 660-670 nm (10-100 mW) (red) and/or 510-540 nm (10-60 mW) (green) for 30-60 mins. An embodiment of this aspect of the invention is wherein the cells are irradiated with 595 nm (20 mW), 635 nm (60 mW) and 535 nm (60 mW), of monochromatic light for 30-60 mins Examples of disorders which can be treated with this further aspect of the invention include the treatment of human diabetic ulcers, in which the combination of particular wavelengths of light are applied to the affected area. While not wishing to be bound to any particular theory, it is thought that the light is activating dermal stem cells in situ in the subject. Further applications of this aspect of the invention include the irradiation of veins in a subject to be treated, as a means of affecting immunomodulatory response. Again while not wishing to be bound to any particular theory, it is thought that the light is activating circulating peripheral stem cells in situ in the subject.

As used herein, "adipose tissue" refers to a tissue containing multiple cell types including adipocytes and microvascular cells. Adipose tissue includes stem cells and endothelial precursor cells. Accordingly, adipose tissue refers to fat including the connective tissue that stores the fat.

As used herein, "processed lipoaspirate" (PLA) refers to tissue, preferably adipose tissue, that has been processed to separate the active cellular component (e.g., the component containing stem cells) from the mature adipocytes and connective tissue. Typically, PLA refers to the pellet of cells obtained by washing and separating the cells from the adipose tissue. The pellet is typically obtained by centrifuging a suspension of cells so that the cells aggregate at the bottom of a centrifuge container.

The aspects of the invention may relate to "activated" stem cells, including ADSC. Stem cells can have two states: "quiescent" in which the cells do not reproduce or double and hence do not provide any differentiated cell lineages. A second state is "activated", which refers to any stem cell triggered to enter a state of reproduction or doubling, and can include a cell entering the cell cycle, cell division, or mitosis and providing cell lineages that differentiate into terminal cell types.

There is now provided a detailed description of how the aspects of the invention can be performed.

Collection of Adipose Tissue

In particular embodiments of the invention disclosed herein, the activated population of stem cells for autologous implantation to a subject are ADSC and are obtained from adipose tissue. Adipose tissue can be obtained by any method known to a person of ordinary skill in the art. For example, adipose tissue may be removed from a patient by suction-assisted lipoplasty, ultrasound-assisted lipoplasty, and excisional lipectomy. In addition, the procedures may include a combination of such procedures, such as a combination of excisional lipectomy and suction-assisted lipoplasty.

As the tissue or some fraction thereof is intended for autologous implantation into a patient the adipose tissue should be collected in a manner that preserves the viability of the cellular component and that minimizes the likelihood of contamination of the tissue with potentially infectious organisms, such as bacteria and/or viruses. Thus, the tissue extraction should be performed in a sterile or aseptic manner to minimize contamination. Suction assisted lipoplasty may be desirable to remove the adipose tissue from a patient as it provides a minimally invasive method of collecting tissue with minimal potential for stem cell damage that may be associated with other techniques, such as ultrasound assisted lipoplasty.

For suction-assisted lipoplastic procedures, adipose tissue is collected by insertion of a cannula into or near an adipose tissue depot present in the patient followed by aspiration of the adipose into a suction device. In one embodiment, a small cannula may be coupled to a syringe, and the adipose tissue may be aspirated using manual force. Using a syringe or other similar device may be desirable to harvest relatively moderate amounts of adipose tissue (e.g., from 0.1 ml to several hundred milliliters of adipose tissue). Procedures employing these relatively small devices have the advantage that the procedures can be performed with only local anaesthesia, as opposed to general anaesthesia. Larger volumes of adipose tissue above this range (e.g., greater than several hundred milliliters) may require general anaesthesia at the discretion of the donor and the person performing the collection procedure. When larger volumes of adipose tissue are desired to be removed, relatively larger cannulas and automated suction devices may be employed in the procedure.

Excisional lipectomy procedures include, and are not limited to, procedures in which adipose tissue-containing tissues (e.g., skin) is removed as an incidental part of the procedure; that is, where the primary purpose of the surgery is the removal of tissue (e.g., skin in bariatric or cosmetic surgery) and in which adipose tissue is removed along with the tissue of primary interest.

The adipose tissue that is removed from a patient is collected into an apparatus for further processing. As discussed herein, and in one embodiment, the apparatus is designed for and dedicated to the purpose of collecting tissue for manufacture of a processed adipose tissue cell population, which includes stem cells and/or endothelial precursor cells. In other embodiments, the apparatus may be any conventional apparatus that is typically used for tissue collection by physicians performing the extraction procedure.

The amount of tissue collected will be dependent on a number of variables including, but not limited to, the body mass index of the donor, the availability of accessible adipose tissue harvest sites, concomitant and pre-existing medications and conditions (such as anticoagulant therapy), and the clinical purpose for which the tissue is being collected. Experience with transplant of hematopoietic stem cells (bone marrow or umbilical cord blood-derived stem cells used to regenerate the recipient's blood cell-forming capacity) shows that engraftment is cell dose-dependent with threshold effects. Thus, it is likely that the general principle that "more is better" will be applied within the limits set by other variables and that where feasible the harvest will collect as much tissue as possible.

It has been discovered that the stem cell percentage of 100 ml of adipose tissue extracted from a lean individual is greater than that extracted from an obese donor. This reflects a dilutive effect of the increased fat content in the obese individual. Therefore, it may be desirable, in accordance with one aspect of the invention, to obtain larger amounts of tissue from overweight donors compared to the amounts that would be withdrawn from leaner patients. This observation also indicates that the utility of this invention is not limited to individuals with large amounts of adipose tissue.

Extraction of Adipose-Derived Stem Cells

In particular embodiments of the invention disclosed herein, preparation of the active cell population will require depletion of the fat-laden adipocyte component of adipose tissue. This is typically achieved by a series of washing and disaggregation steps in which the tissue is first rinsed to reduce the presence of free lipids (released from ruptured adipocytes) and peripheral blood elements (released from blood vessels severed during tissue harvest), and then disaggregated to free intact adipocytes and other cell populations from the connective tissue matrix. In certain embodiments, the entire adipocyte component, or non-stem cell component, is separated from the stem cell component of the adipose tissue. In other embodiments, only a portion or portions of the adipocyte component is separated from the stem cells. Thus, in certain embodiments, the stem cells can be administered with endothelial precursor cells.

Rinsing is an optional step in which the tissue is mixed with solutions to wash off free lipid and single cell components, such as those components in blood, leaving behind intact adipose tissue fragments. In one embodiment, the adipose tissue that is removed from the patient is mixed with isotonic saline. Intact adipose tissue fragments can be separated from the free lipid and cells by any means known to persons or ordinary skill in the art including, filtration, decantation, sedimentation, or centrifugation.

The intact tissue fragments are then disaggregated using any conventional techniques or methods, including mechanical force (mincing or shear forces), enzymatic digestion with single or combinatorial protelolytic enzymes, such as collagenase, trypsin, lipase, liberase H1, as disclosed in U.S. Pat. No. 5,952,215, and pepsin, or a combination of mechanical and enzymatic methods. For example, the cellular component of the intact tissue fragments may be disaggregated by methods using collagenase-mediated dissociation of adipose tissue, similar to the methods for collecting microvascular endothelial cells in adipose tissue, as disclosed in U.S. Pat. No. 5,372,945. Additional methods using collagenase that may be used in practicing the invention are disclosed in U.S. Pat. Nos. 5,830,714 and 5,952,215, and by Williams, S. K., S. McKenney, et al. (1995), Cell Transplant 4(3): 281-9. Similarly, a neutral protease may be used instead of collagenase, as disclosed in Twentyman, P. R. and J. M. Yuhas (1980), Cancer Lett 9(3): 225-8. Furthermore, methods of the invention may employ a combination of enzymes, such as a combination of collagenase and trypsin, as disclosed in Russell, S. W., W. F. Doe, et al. (1976), Int J Cancer 18(3): 322-30; or a combination of an enzyme, such as trypsin, and mechanical dissociation, as disclosed in Engelholm, S. A., M. Spang-Thomsen, et al. (1985), Br J Cancer 51(1): 93-8.

In a preferred embodiment, the intact tissue fragments are disaggregated using mechanical force (mincing and shear forces), enzyme digestion and soy bean lecithin.

The active cell population (processed lipoaspirate) may then be obtained from the disaggregated tissue fragments by reducing the presence of lipid-containing adipocytes. Embodiments may employ the use of gravity or a vacuum while maintaining a closed system. Separation of the cells in the suspension may be achieved by buoyant density sedimentation, centrifugation, elutriation, differential adherence to and elution from solid phase moieties, antibody-mediated selection, differences in electrical charge; immunomagnetic beads, fluorescence activated cell sorting (FACS), or other means. Examples of these various techniques and devices for performing the techniques may be found in Hemstreet, G. P., 3rd, P. G. Enoch, et al. (1980), Cancer Res 40(4): 1043-9; Schweitzer, C. M., van, et al. (1995), Exp Hematol 23(1): 41-8; Gryn, J., R. K. Shadduck, et al. (2002), J Hematother Stem Cell Res 11(4): 719-30; Prince, H. M., J. Bashford, et al. (2002), Cytotherapy 4(2): 137-45; Watts, M. J., T. C. Somervaille, et al. (2002), Br J Haematol 118(1): 117-23; Mainwaring, G. and A. F. Rowley (1985), Cell Tissue Res 241(2): 283-90; Greenberg, A. W. and D. A. Hammer (2001), Biotechnol Bioeng 73(2): 111-24; and U.S. Pat. Nos. 6,277,060; 6,221,315; 6,043,066; 6,451,207; 5,641,622; and 6,251,295. In the an embodiment, the cells in the suspension are separated from the cellular component of the suspension using a centrifuge. In one such exemplary embodiment, the cell collection container may be a flexible bag that is structured to be placed in a centrifuge (e.g., manually or by robotics). In other embodiments, a flexible bag is not used.

After centrifugation, the cellular component forms a pellet, which may then be resuspended with a buffered solution with or without stimulatory growth factors.

In one particular embodiment, the tissue is incubated with collagenase at a collagenase concentration, temperature, and time sufficient to provide adequate disaggregation, and then a soy lecithin composition is used, at a preferred concentration, temperature and time sufficient for further removal of lipid-containing cells. In a preferred embodiment, the collagenase enzyme used will be approved for human use by the relevant authority (e.g., the U.S. Food and Drug Administration). Suitable collagenase preparations include recombinant and non-recombinant collagenase. Non-recombinant collagenase may be obtained from F. Hoffmann-La Roche Ltd, Indianapolis, Ind. and/or Advance Biofactures Corp., Lynbrook, N.Y. Recombinant collagenase may also be obtained as disclosed in U.S. Pat. No. 6,475,764.

In one embodiment, solutions contain lecithin are incubated at from about 30° C. to about 38° C. for from about 5 minutes to about 30 minutes. These parameters will vary according to the source of the lecithin, in order to validate that the system is effective at extracting the desired cell populations in an appropriate time frame.

A particular preferred concentration, time and temperature is 20 ng/ml collagenase (Blendzyme 1, Roche) incubated for 45 minutes, at about 37° C. the lecithin composition incubated for 15 min at about 37° C. The collagenase and lecithin used should be free of micro-organisms and contaminants, such as endotoxin.

Following disaggregation the active cell population may be washed/rinsed to remove additives and/or by-products of the disaggregation process (e.g., collagenase, lecithin and newly-released free lipid). The active cell population could then be concentrated by centrifugation or other methods known to persons of ordinary skill in the art, as discussed above. These post-processing wash/concentration steps may be applied separately or simultaneously.

In addition to the foregoing, there are many post-wash methods that may be applied for further purifying the active cell population. These include both positive selection (selecting the target cells), negative selection (selective removal of unwanted cells), or combinations thereof.

In one embodiment, a solid phase material with adhesive properties selected to allow for differential adherence and/or elution of a subpopulation of cells within the processed lipoaspirate is inserted into the system after the cell washing step. This general approach has been performed in clinical blood transfusion in which filters differentially capturing leukocytes are used to deplete transfused red cells of contaminating white blood cell (Soli, M., et al., 2001, Vox Sang 81(2): p. 108-12; Smith, J. W., Apheresis, 1997, Ther Apher. 1(3): p. 203-6). Filters of this type are distributed by Pall Bedical (Leukogard RS and Purecell RCQ) and Asahi (RS2000). Differential adherence has also been applied to positive selection of monocytes (Berdel, W. E., et al., 1982, Immunobiology 163(5): p. 511-20) and epidermal stem cells (Bickenbach, J. R. and E. Chism, 1998, Exp Cell Res. 244(1): p. 184-95).

An alternate embodiment of this differential adherence approach would include use of antibodies and/or combinations of antibodies recognizing surface molecules differentially expressed on target and unwanted cells. Selection on the basis of expression of specific cell surface markers (or combinations thereof) is another commonly applied technique in which antibodies are attached (directly or indirectly) to a solid phase support structure (Geiselhart, A., et al., 1996, Nat Immun 15(5): p. 227-33; Formanek, M., et al., 1998, Eur Arch Otorhinolaryngol. 255(4): p. 211-5; Graepler, F., U. Lauer, and M. Gregor, 1998, J Biochem Biophys Methods. 36(2-3): p. 143-55; Kobari et al., 2001, J Hematother Stem Cell Res., 10(2): p. 273-81; Mohr, M., et al., 2001, Clin Cancer Res. 7(1): p. 51-7; Pugh, R. E., et al., 1998, J Hematother, 1998. 7(2): p. 159-68). This approach has obvious applications in both positive and negative selection in which, for example, residual white blood cells might be removed by use of the CD45 antibody). Similarly, Reyes et al have applied a complex blend of antibodies in the selection of a multipotential adult progenitor cell from human bone marrow (Reyes, M., et al. 2001, Blood. 98(9): p. 2615-25). For example, an antibody such as AP2 (Joyner, C. J., et al., 1999, Pathol Res Pract. 195(7): p. 461-6) which specifically binds to adipocytic cells could be employed to preferentially deplete residual adipocytic cells (including immature adipocytes and adipoblasts). Positive selection could be applied by use of antibodies specific for the target cell population(s). For example, Quirici et al have used antibodies to the Nerve Growth Factor Receptor to enrich bone marrow-derived mesenchymal stem cells (Quirici, N., et al., 2002, Exp Hematol. 30(7): p. 783-91).

In one embodiment of an antibody-based approach, an antibody (for example AP2) or a cocktail of antibodies (for example AP2, CD3, CD19, CD11b) would be added to the processed lipoaspirate. Many other antibodies and combinations of antibodies will be recognized by one skilled in the art and these examples are provided by way of example only. After incubation, under conditions pre-determined to allow for optimal binding of these antibodies to their cognate antigens, the cells would be washed by passing through the spinning membrane filter or other embodiment of the cell washing chamber to remove unbound, excess antibody. The cells would then be passed over a solid phase structure similar to that described in the embodiment above but in which the solid phase has attached a secondary antibody capable of high affinity attachment to the primary antibodies now bound to the cell surface. Target cells, for example the adipose tissue-derived stem cell, would pass freely through this filter by virtue of the absence of expression of cell surface antigens recognized by the selected antibody (antibody cocktail) thereby creating a negative selection system.

An antibody-mediated positive selection embodiment could be achieved in very similar fashion by including a third additive that facilitates detachment of the cells from the solid phase support. In this embodiment, the enzyme papain or cymopapain could be added to cleave the antibody molecules and release cells from the solid phase support (Civin, C. I., et al., 1990, Prog Clin Biol Res. 333(387): p. 387-401; discussion 402). Another alternative would be the use of specific peptides that would compete with the cell surface antigen for binding to the antibodies, as described by Tseng-Law et al, U.S. Pat. No. 6,017,719.

In another embodiment the cell pellet could be resuspended, layered over (or under) a fluid material formed into a continuous or discontinuous density gradient and placed in a centrifuge for separation of cell populations on the basis of cell density. Examples of media suitable for formation of such gradients include Percoll and Ficoll-Paque (Qian, X., L. Jin, and R. V. Lloyd, 1998, Endocr Pathol. 9(1): p. 339-346; Smits, G., W. Holzgreve, and S. Hahn, 2000, Arch Gynecol Obstet. 263(4): p. 160-3) or Ficoll-Paque (Lehner, M. and W. Holter, 2002, Int Arch Allergy Immunol. 128(1): p. 73-6). Van Merris et al, (Van Merris, V., et al., 2001, Vet Immunol Immunopathol. 83(1-2): p. 11-7) employed a discontinuous three-step Percoll gradient to separate bovine myeloid cells according to their maturation state on this basis. This embodiment would be capable of separating out certain residual blood cell populations and immature adipocytes (pre-adipocytes) from the cell population.

In a similar embodiment continuous flow approaches such as apheresis (Smith, J. W., Apheresis supra) and elutriation (with or without counter-current) (Lasch, J., G. Kullertz, and J. R. Opalka, 2000, Clin Chem Lab Med. 38(7): p. 629-32; Ito, Y. and K. Shinomiya, 2001, J Clin Apheresis. 16(4): p. 186-91; Dlubek, D., et al., 2002, Eur J Haematol. 68(5): p. 281-8) may also be employed. Such mechanisms have been used to fractionate blood cells, including separation of red blood cells on the basis of age (Lasch, J., G. Kullertz, and J. R. Opalka, supra) and application of this general approach to further purification of cells of interest from processed lipoaspirate will be readily apparent to one skilled in the art. This embodiment may require modification of the apparatus used to practice the method of the invention such that the apparatus would be integrated with a device providing the apheresis or elutriation capability.

Adherence to plastic followed by a short period of cell expansion has also been applied in bone marrow-derived adult stem cell populations (Jaiswal, N., et al., 1997, J Cell Biochem. 64(2): p. 295-312; Hou, L., et al., 2002, Zhonghua Xue Ye Xue Za Zhi 23(8): p. 415-9). This approach uses culture conditions to preferentially expand one population while other populations are either maintained (and thereby reduced by dilution with the growing selected cells) or lost due to absence of required growth conditions. Sekiya et al have described conditions which might be employed in this regard for bone marrow-derived stem cells (Sekiya, I., et al., 2002, Stem Cells 20(6): p. 530-41). This approach (with or without differential adherence to the tissue culture plastic) could be applied to a further embodiment of this invention. In this embodiment the cells are removed from the apparatus used for the method of the invention and placed into a further device providing the cell culture component. This could be in the form of a conventional laboratory tissue culture incubator or a Bioreactor-style device such as that described by Tsao et al, U.S. Pat. No. 6,001,642, or by Armstrong et al, U.S. Pat. No. 6,238,908.

Activation of the Preparation of Stem Cells

Subsequent to the preparation of a concentrated population of stem cells, the cell population isolated is activated by irradiating the cells with certain frequencies of wavelengths in the visible light spectrum (400-1200 nm) to stimulated growth and differentiation of stem cells. Light irradiation or photomodulation can be utilized for significant benefit in the stimulation of proliferation, growth, differentiation, of stem cells from any living organism. Stem cells growth and differentiation into tissues or organs or structures or cell cultures for infusion, implantation, etc (and their subsequent growth after such transfer) can be facilitated or enhanced or controlled or inhibited. The origin of such stem cells can be from any living tissue or organism. In humans stem cells for these embodiments may come from any source in the human body, but typically originate from the bone marrow, blood, adipose-tissue, embryo, placenta, fetus, umbilical cord or cord blood, and can be either naturally or artificially created either in vivo, ex vivo or in vitro with or without genetic alteration or manipulation or engineering. Such tissue can come from any living source of any origin.

Stem cells can be photoactivated or photoinhibited by photomodulation. There is little or no temperature rise with this process although transient local nondestructive intracellular thermal changes may contribute via such effects as membrane changes or structured conformational changes.

The wavelength or bandwidth of wavelengths is one of the critical factors in selective photomodulation. Pulsed or continuous exposure, duration and frequency of pulses (and dark 'off' period) and energy are also factors as well as the presence, absence or deficiency of any or all cofactors, enzymes, catalysts, or other building blocks of the process being photomodulated.

Photomodulation can control or direct the path or pathways of differentiation of stem cells, their proliferation and growth, their motility and ultimately what they produce or secrete and the specific activation or inhibition of such production.

Photomodulation can up-regulate or down-regulate a gene or group of genes, activate or inactivate enzymes, modulate DNA activity, and other cell regulatory functions.

The selection of wavelength photomodulation is important as is the bandwidth selected as there may be a very narrow bandwidth for some applications—in essence these are biologically active spectral intervals. Generally the photomodulation will target flavins, cytochromes, iron-sulfur complexes, quinines, heme, enzymes, and other transition metal ligand bond structures though not limited to these.

These act much like chlorophyll and other pigments in photosynthesis as 'antennae' for photo acceptor molecules. These photo acceptor sites receive photons from electromagnetic sources such as these described in this application, but also including radio frequency, microwaves, electrical stimulation, magnetic fields, and also may be affected by the state of polarization of light. Combinations of electromagnetic radiation sources may also be used.

The photon energy being received by the photo acceptor molecules from even low intensity light therapy (LILT) is sufficient to affect the chemical bonds thus 'energizing' the photo acceptor molecules which in turn transfers and may also amplify this energy signal. An 'electron shuttle' transports this to ultimately produce ATP (or inhibit) the mitochondria thus energizing the cell (for proliferation or secretory activities for example). This can be broad or very specific in the cellular response produced. The health of the cells and their environment can greatly affect the response to the photo modulation. Examples include hypoxia, excess or lack or ration of proper cofactors or growth factors, drug exposure (eg. reduced ubiquinone from certain anticholesterol drugs) or antioxidant status, diseases, etc. This is another circumstance wherein oral or systemic replacement of such agents or factors may be used to enhance the photomodulation effects. It should be also noted that any process which causes the accumulation of such agents, or conversely accelerates the inactivation or removal of inhibitors of such agents, would have as a net outcome the effect of increasing the concentration of these agents without directly adding such agents.

The mechanism, which establishes 'priorities' within living cells, can be photomodulated. This can include the differentiation of early embryos or stem cell population. Exogenous light activated chromophores may also be used alone or in combination with exogenous chromophores. Genetically altered or engineered stem cells or stem cells which have an inborn genetic error or defect or uncommon but desirable or beneficial trait may require a different 'combination' of parameters than their analogous 'normal' stem cells or may produce different cellular response if use the same combination of parameters. Using various methods of photomodulation or other techniques known in the art more specific cellular effects may be produced by 'blocking' some 'channels' that are photomodulated.

In the preferred embodiment, the sources of said monochromatic electromagnetic light could be derived from a light emitting diode, a laser, a fluorescent light source, an organic light emitting diode, a light emitting polymer, a xenon arc lamp, a metal halide lamp, a filamentous light source, an intense pulsed light source, a sulphur lamp, and combinations thereof. The preferred embodiment would be to irradiate the stem cell population with a combination of laser diodes emitting light wavelengths and power ratings: 575-595 nm (5-20 mW) (yellow; this can also be considered to be an "orange" range of wavelengths as well), and 630-635 nm or 660-670 nm (10-100 mW) (red) and/or 510-540 nm (10-60 mW) (green) for 30-60 mins, where the sample is placed at a distance of 0-30 cm. More preferably the stem cells are irradiated with 595 nm (20 mW), 635 nm (60 mW) and 535 nm (60 mW), of monochromatic light for 30-60 mins. An example of an apparatus which can be used to irradiate stem cells is provided in the accompanying figures.

The stem cells prepared according to the method of the invention can also be activated using growth factors that are known to stimulated growth and differentiation of stem cells. Hence an embodiment of the invention is wherein the stem cells are exposed to one or more growth factors.

The growth factors can be obtained from a variety of sources: synthetic peptides; recombinant protein manufacture methods; secretions of cultured cells; and human or animal tissues. Examples of growth factors which can be used in this embodiment of the invention include Epidermal Growth Factor (EGF); Platelet-Derived Growth Factor (PDGF); Fibroblast Growth Factor (FGFs); Transforming Growth Factors-b (TGFs-b); Transforming Growth Factor-a (TGF-a); Erythropoietin (EPO); Insulin-like Growth Factor-I (IGF-I); Insulin-like Growth Factor-II (IGF-II); Interleukin-1 (IL-1); Interleukin-2 (IL-2); Interleukin-3 (IL-3); Interleukin-6 (IL-6); Interleukin-8 (IL-8); Tumour Necrosis Factor-a (TNF-a); Tumour Necrosis Factor-b (TNF-b); Interferon-g (INF-g); Colony Stimulating Factors (CSFs). Such growth factors are well known in the art and can be readily obtained by the skilled person, either from commercial suppliers of such peptides, or using commonly applied techniques to appropriate biological materials.

Preferably the growth factors are less than 50,000 MW molecules, isolated from porcine fetal mesenchymal stem cell culture media/secretions. Analysis of the media by MS/MS showed the following growth factor peptides: Epidermal Growth Factor (EGF); Platelet-Derived Growth Factor (PDGF); Fibroblast Growth Factor (FGFs); Transforming Growth Factors-b (TGFs-b); Erythropoietin (EPO); Insulin-like Growth Factor-I (IGF-I); Insulin-like Growth Factor-II; Tumour Necrosis Factor-a (TNF-a).

An embodiment of the invention is wherein the growth factors are provided by platelet-rich plasma prepared from the patient to be treated.

Wound healing is a complex process, involving a mechanism of complex cascading regulatory events at both the molecular and cellular levels. Growth factors (GFs) are secreted by a wide variety of cells to regulate the wound healing process in an orderly manner. Over the last decade, various GFs, including platelet-derived growth factor (PDGF), and transforming growth factor-beta (TGF-β), have been used to accelerate the healing process.

Platelet-rich plasma (PRP), as a storage vehicle of growth factors, is a new application of tissue engineering which was considered for the application of growth factors. PRP is a concentration of platelets in plasma developed by gradient density centrifugation. It contains many growth factors, such as PDGF, TGF-β, vascular endothelial growth factor (VEGF), epidermal growth factor (EGF), insulin-like growth factor (IGF), etc, and it has been successfully used in a variety of clinical applications for improving hard and soft tissue healing. Platelet-rich plasma has also been shown to enhance the proliferation of human adipose-derived stem cells.

We provide a protocol below for preparing platelet-rich plasma from the patient to be treated. Blood would be obtained during or just prior to the patient's adipose tissue extraction procedure. The method is as follows:

1. Place blood (20-100 ml) in sterile, anticoagulant containing tubes.
2. Mix by inverting all tubes 8-10 times.
3. Centrifuge tubes at 72×g for 15 minutes.
4. Aspirate top layer (i.e. plasma layer) and transfer aspirate to sterile tubes.
5. Centrifuge aspirate at 1000×g for 5 minutes.
6. Aspirate plasma to leave a total of 10 ml of plasma with cell pellet.
7. Resuspend pellet.
8. Irradiate suspension in tubes with Adistem Laser (described below) for 30 min
9. Centrifuge at 100 g for 5 min
10. Keep the aspirate.

The stem cells is then mixed with the aspirate and incubated at 30-38° C. (37° C.) for 5-120 min (30 min)

The growth factor components of platelet-rich plasma includes: PDGF (Platelet derived growth factor); TGF-αβ (Transforming growth factor alpha & beta); EGF (Epidermal growth factor) FGF (Fibroblast growth factor); IGF (Insulin growth factor); PDEGF (platelet derived epidermal growth factor); PDAF (platelet derived angiogenesis factor); IL-8 (Interleuking-8); TNF-a (Tumor necrosis factor alpha); CTGR (Connective tissue growth factor) GM-CSF (Granulocyte macrophage colony stimulating factor); KGF (Keratinocyte growth factor). The platelet-rich plasma also includes high concentration of leukocytes (neutrophils, eosinophils) for microbicidal events; high concentration of wound macrophages and other phagocytic cells, for biological debridement; istamines, Serotonin, ADP, Thromboxane A2, and other vasoactive and chemotactic agents; high platelet concentration and native fibrinogen concentration for improved hemostasis.

In another embodiment, the stem cell population isolated is activated with both growth factors and light irradiation to stimulate growth and differentiation of the stem cells.

The preferred embodiment would be to use the patient's own platelet derived growth factors and combination of light frequencies as described above.

Administration of Cells

In certain embodiments, the activated stem cell population is administered directly into the patient. In other words, the activated cell population are administered to the patient.

The activated cells that have been concentrated and activated, as described above, may be administered to a patient without further processing, or may be administered to a patient after being mixed with other tissues or cells. In certain embodiments, where the stem cells are ADSC the concentrated activated cells are mixed with adipose tissue that has not been similarly processed. Thus, by practicing embodiments of the methods of the invention, a composition comprising adipose tissue with an enhanced concentration of active cells may be administered to the patient. The volumes of the various adipose tissue may be different.

In other embodiments, at least a portion of the activated cell population is stored for later implantation/infusion. The population may be divided into more than one aliquot or unit such that part of the population of stem cells is retained for later application while part is applied immediately to the patient. Moderate to long-term storage of all or part of the cells in a cell bank is also within the scope of this invention, as disclosed in U.S. patent application Ser. No. 10/242,094, entitled PRESERVATION OF NON EMBRYONIC CELLS FROM NON HEMATOPOIETIC TISSUES, filed Sep. 12, 2002, which claims the benefit of U.S. Provisional Patent Application 60/322,070 filed Sep. 14, 2001, which is commonly assigned, and the contents of which are expressly incorporated herein by reference. In such an embodiment, the activated cells may be mixed with one or more units of fresh or preserved tissue to provide a composition containing the stem cells at a higher concentration than a unit of tissue prior to processing.

At the end of processing, the concentrated and activated cells may be loaded into a delivery device, such as a syringe, for placement into the recipient by intradermal, subcutaneous, intravenous, intramuscular, or intraperitoneal techniques. In other words, cells may be placed into the patient by any means known to persons of ordinary skill in the art, for example, they may be injected into blood vessels for systemic or local delivery, into tissue (e.g., cardiac muscle, or skeletal muscle), into the dermis (subcutaneous), into tissue space (e.g., pericardium or peritoneum), or into tissues (e.g., periurethral emplacement), or other location. Preferred embodiments include placement by needle or catheter, or by direct surgical implantation in association with additives such as a preformed matrix.

The activated cell population may be applied alone or in combination with other cells, tissue, tissue fragments, demineralized bone, growth factors such as insulin or drugs such as members of the thiaglitazone family, biologically active or inert compounds, resorbable plastic scaffolds, or other additive intended to enhance the delivery, efficacy, tolerability, or function of the population. The activated cell population may also be modified by insertion of DNA or by placement in cell culture in such a way as to change, enhance, or supplement the function of the cells for derivation of a cosmetic, structural, or therapeutic purpose. For example, gene transfer techniques for stem cells are known by persons of ordinary skill in the art, as disclosed in Mosca, J. D., J. K. Hendricks, et al., 2000, Clin Orthop 379 Suppl: S71-90, and may include viral transfection techniques, and more specifically, adeno-associated virus gene transfer techniques, as disclosed in Walther, W. and U. Stein, 2000, Drugs 60(2): 249-71, and Athanasopoulos, T., S. Fabb, et al., 2000, Int J Mol Med 6(4): 363-75. Non-viral based techniques may also be performed as disclosed in Muramatsu, T., A. Nakamura, et al., 1998, Int J Mol Med 1(1): 55-62.

In one aspect, where the stem cells are ADSC the activated ADSC could be mixed with unprocessed fragments of adipose tissue and placed back into the recipient using a very large gauge needle or liposuction cannula. Transfer of autologous fat without supplementation with processed cells is a common procedure in plastic and reconstructive surgery. However, results can be unpredictable as the transferred material tends to rapidly reabsorb resulting in an unstable graft. Activated Adipose tissue-derived cells of the invention that are, for example, substantially depleted of mature adipocytes may provide an environment that supports prolonged survival and function of the graft.

In another aspect, the activated stem cell population could be placed into the recipient and surrounded by a resorbable plastic sheath such as that manufactured by MacroPore Biosurgery, Inc. (U.S. Pat. Nos. 6,269,716 and 5,919,234). In this setting the sheath would prevent prolapse of muscle and other soft tissue into the area of a bone fracture thereby allowing the emplaced processed adipose tissue-derived cells to promote repair of the fracture. In this aspect, the beneficial effect might be enhanced by supplementation with additional components such as pro-osteogenic protein growth factors or biological or artificial scaffolds.

In another aspect, the activated cells could be combined with a gene encoding a pro-osteogenic growth factor which would allow cells to act as their own source of growth factor during bone healing or fusion. Addition of the gene could be by any technology known in the art including but not limited to adenoviral transduction, "gene guns," liposome-mediated transduction, and retrovirus or lentevirus-mediated transduction.

Particularly when the activated cells and/or tissue containing the cells are administered to a patient other than the patient from which the cells and/or tissue were obtained, one or more immunosuppressive agents may be administered to the patient receiving the cells and/or tissue to reduce, and preferably prevent, rejection of the transplant. Examples of immunosuppressive agents suitable with the methods disclosed herein include agents that inhibit T-cell/B-cell co stimulation pathways, such as agents that interfere with the coupling of T-cells and B-cells via the CTLA4 and B7 pathways, as disclosed in U.S. Patent Pub. No. 20020182211. Other examples include cyclosporin, myophenylate mofetil, rapamicin, and anti-thymocyte globulin.

In certain embodiments of the invention, the activated cells are administered to a patient with one or more cellular differentiation agents, such as cytokines and growth factors. Examples of various cell differentiation agents are disclosed in Gimble, J. M., C. Morgan, et al. (1995) J Cell Biochem 58(3): 393-402; Lennon, D. P., S. E. Haynesworth, et al. (1995), Exp Cell Res 219(1): 211-22; Majumdar, M. K., M. A. Thiede, et al. (1998), J Cell Physiol 176(1): 57-66; Caplan, A. I. and V. M. Goldberg (1999), Clin Orthop (367 Suppl): S12-6; Ohgushi, H. and A. I. Caplan (1999), J Biomed Mater Res 48(6): 913-27; Pittenger, M. F., A. M. Mackay, et al. (1999) Science 284(5411): 143-7; Caplan, A. I. and S. P. Bruder (2001), Trends Mol Med 7(6): 259-64; Fukuda, K. (2001), Artif Organs 25(3): 187-93; Worster, A. A., B. D. Brower-Toland, et al. (2001), J Orthop Res 19(4): 738-49; Zuk, P. A., M. Zhu, et al. (2001), Tissue Eng 7(2): 211-28; and Mizuno, H., P. A. Zuk, et al. (2002), Plast Reconstr Surg 109(1): 199-209; discussion 210-1.

By administering the activated cells to a patient, one can treat numerous diseases, including, and not limited to, bone-related disorders, diseases, or injuries, including slow/non-union fractures, osteoporosis (age-related or chemotherapy-induced), inherited diseases of bone (osteogenesis imperfecta); adipose related disorders or diseases; liver related diseases, disorders, or injuries, including liver failure, hepatitis B, and hepatitis C; myocardial infarctions, including heart attack or chronic heart failures; renal diseases or kidney damage; retinal diseases or damage or necrosis; wound healing (e.g., from surgery or diabetic ulcers); skeletal muscle disorders both traumatic and inherited; cartilage and joint repair both traumatic and autoimmune; lung injuries; diabetes; intestinal disorders; nervous system disorders, diseases, or injuries, such as central nervous systems disorders, diseases, or injuries, including spinal cord injuries, Parkinson's disease, Alzheimer's disease, and stroke.

The activated stem cells may also be administered to a patient for cosmetic purposes, such as by enhancing or improving physical features, including reducing wrinkles, enhancing organ mass, and the like.

Many other conformations of the staged mechanisms used for cell processing will be apparent to one skilled in the art and the present description is included as one example only. For example, mixing of tissue and saline during washing and disaggregation may occur by agitation as in the present example or by fluid recirculation. Cell washing may be mediated by a continuous flow mechanism such as the spinning membrane approach, differential adherence, differential centrifugation (including, but not limited to differential sedimentation, velocity, or gradient separation), or by a combination of means. Similarly, additional components to allow further manipulation of cells including addition of growth factors or other biological response modifiers (Lind, M., (1998) Acta Orthop Scand Suppl, 1998. 283: p. 2-37; Hanada, K., J. E. Dennis, and A. I. Caplan, (1997) J Bone Miner Res. 12(10): p. 1606-14; Lieberman, J. R., et al., (1998) J Orthop Res. 16(3): p. 330-9), mixing of cells with other structural components (e.g., bone fragments (Jean, J. L., S. J. Wang, and M. K. Au (1997) J Formos Med Assoc 96(7): p. 553-7), collagen (Saadeh, P. B., et al., (2001) J Craniofac Surg. 12(6): p. 573-579) and/or synthetic components intended for implant with the cells into the recipient (Petite, H., et al., (2000) Nat Biotechnol., 18(9): p. 959-63. taf/dynapage.taf?file=/ncb/biotech/v18/n9/full/nbt0900.sub.--959.html taf/dynapage.taf?file=/ncb/biotech/v18/n9/abs/nbt0900.sub.--959.html; Gao, J., et al., (2001) Tissue Eng. 7(4): p. 363-71; Ohgushi, H. and A. I. Caplan, supra; Caplan, A. I. and V. M. Goldberg, supra). Post-processing manipulation may also include cell culture (Caplan, A. I. and S. P. Bruder, supra; Petite, supra; Zuk, P. A., et al., 2001 supra) gene transfer (Luskey, B. D., et al. (1990) Ann N Y Acad Sci. 612(398): p. 398-406; Grompe, M., et al. (1998) J Inherit Metab Dis. 21(5): p. 518-31; Gazit, D., et al. (1999) J Gene Med. 1(2): p. 121-33; Mosca, J. D., et al., supra), or further cell purification (Greenberg, A. W. and D. A. Hammer, 2001 supra; Mainwaring, G. and A. F. Rowley, 1985 supra; Schweitzer, C. M., et al., 1995 supra).

In additional embodiments of the invention relating to ADSC, tissue collected into a conventional adipose tissue trap could be transferred into a processing set designed for processing other tissues. For example, Baxter Inc. manufacture and sell a series of plastic bags and filters intended for use in the setting of a bone marrow transplant harvest ("Bone Marrow Collection Kit with Flexible Pre-Filters and Inline Filters", Product Code, 4R2107, U.S. Pat. Nos. 4,346,703 and 5,724,988). This bag set contains a large conical bag with an integrated 800 μm filter which could be used for washing the collected adipose tissue. In this example adipose tissue fragments larger than 800 μm would be retained in the bag. These fragments could then be washed by repeated addition of saline (or other washing solution) followed by removal of waste material through ports below the filter. Mixing could be achieved manually or by use of a benchtop rocking device and warming could be applied by use of a heating pad. Disaggregation could occur within the lumen of this bag. Following disaggregation cells would pass through the integrated 800 μm filter (and optionally through one or more filters of smaller mesh size provided with the kit) and collected into a collection bag (also provided). This bag could then be placed into a centrifuge (e.g., a Sorval RC-3C) where cells could be serially washed and concentrated. Cells could also be washed using existing cell washing devices (largely developed for washing human blood products) such as those sold by Baxter Inc (Cytomate or Baxter CS3000) or by Cobe Inc. (Cobe Spectra). The disposable elements may be integrated using the fittings provided by the manufacturer or they may be linked by use of a sterile connecting device such as those manufactured by Terumo Inc. Similarly the mechanisms described in this less integrated approach could be linked to a central controller and assembled as components of a more integrated device. A peristaltic pump or battery of pumps could be used to automate fluid flow with use of manual or automated clamping to open and close fluid pathways.

Alternatively, a plastic bag (similar to an i.v. saline bag) with various inlets similar to what they use for placental cord blood can be used in the method of the invention, for example bags available from a company called Fresenius.

In a preferred embodiment of the invention, the tissue removal system and processing set would be present in the vicinity of the patient receiving the treatment, such as the operating room or out-patient procedure room (effectively at the patient's bedside). This allows rapid, efficient tissue harvest and processing, alleviating the opportunity for specimen handling/labeling error and thereby allow for performance of the entire process in the course of a single surgical procedure.

Once prepared, the activated stem cells can be labelled prior to administration to a subject. This allows a physician to determine to location of the administered cells in the patient once administered. Preferably the activated stem cells are labelled with 99Tc HMPAO; an experimental protocol for ADSC labelling is provided in the accompanying examples.

A further aspect of the invention provides an apparatus for the preparation of a population of stem cells for autologous implantation, said apparatus comprising:

i) a tissue preparation container including a one way inlet port structured to receive tissue removed from a patient and for the administration of at least one additive to mix with the stem cells contained therein;

ii) an outlet structured to permit the cells in the container to be removed.

A preferred embodiment of the apparatus of the invention is wherein the apparatus includes means for mechanically disrupting the tissue. Preferably the apparatus also includes means for separating, and optionally concentrating, the stem cells from further components of the tissue.

A further preferred embodiment of this aspect of the invention is wherein the apparatus further comprises:
  i) one or more sources of wavelengths of yellow and red and/or green light; and,
  ii) a locator for arranging a population of cells in the said wavelengths of light.

A further aspect of the invention provides an apparatus for preparing an activated population of stem cells for autologous implantation to a subject, comprising:
  i) one or more sources of wavelengths of yellow and red and/or green light; and,
  ii) a locator for arranging a population of cells in the said wavelengths of light.

In the apparatus of the aspects of the invention, it is preferred that the wavelengths are 575-595 nm (5-20 mW), and 630-635 nm or 660-670 nm (10-100 mW) and/or 510-540 nm (10-60 mW) of monochromatic light; most preferably 595 nm (20 mW), 635 nm (60 mW) and 535 nm (60 mW) of monochromatic light.

Also, in the apparatus of the aspects of the invention, it is preferred that the stem cells are ADSC and where appropriate the tissue is adipose tissue.

The following examples are provided to demonstrate particular situations and settings in which this technology may be applied and are not intended to restrict the scope of the invention and the claims included in this disclosure FIG. 1: A schematic diagram of the procedure for autologous implantation of activated ADSC.

FIG. 2: Details of the ADSC harvested by the procedures disclosed herein.

Figure 3:
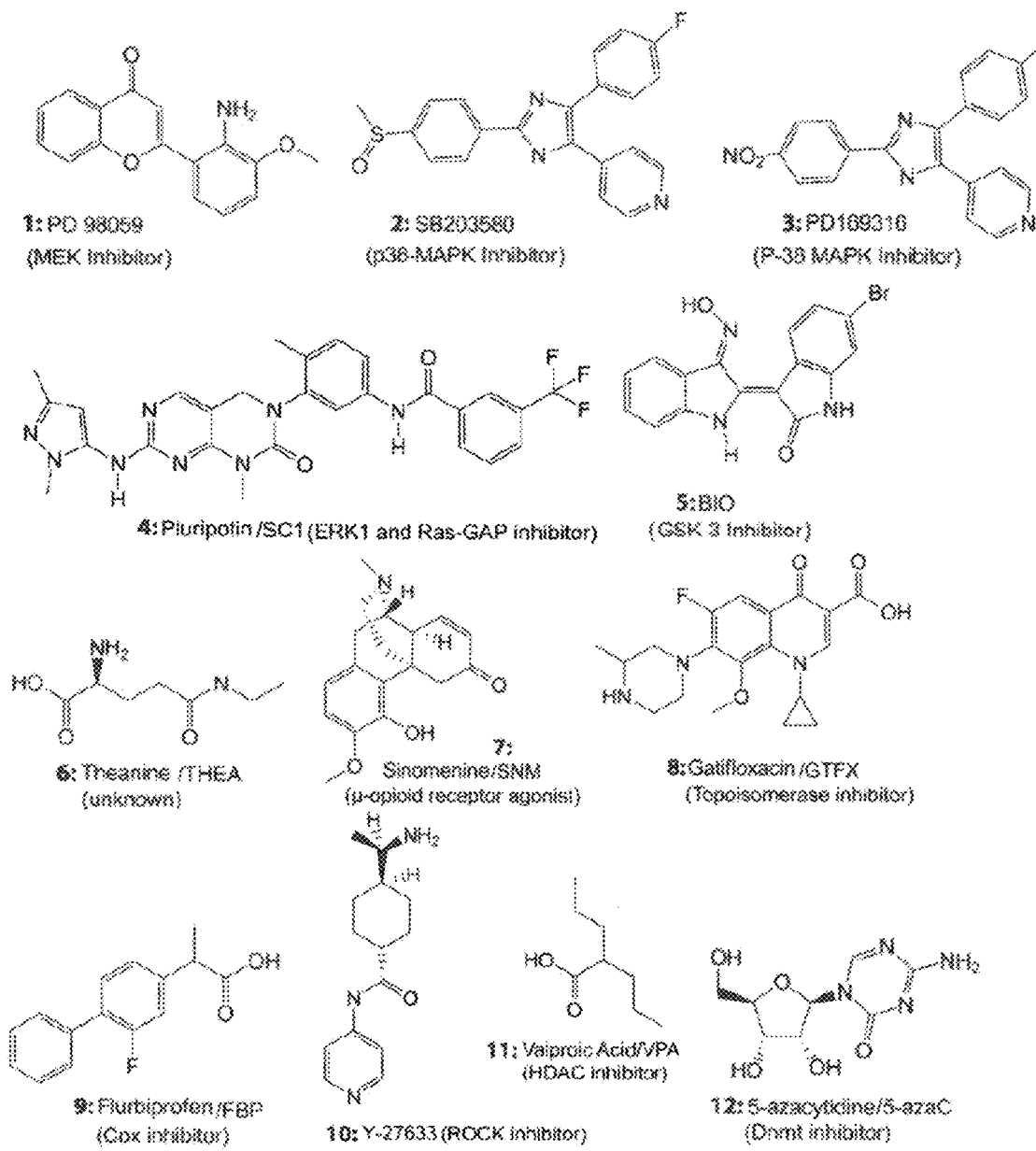
Figure 3:
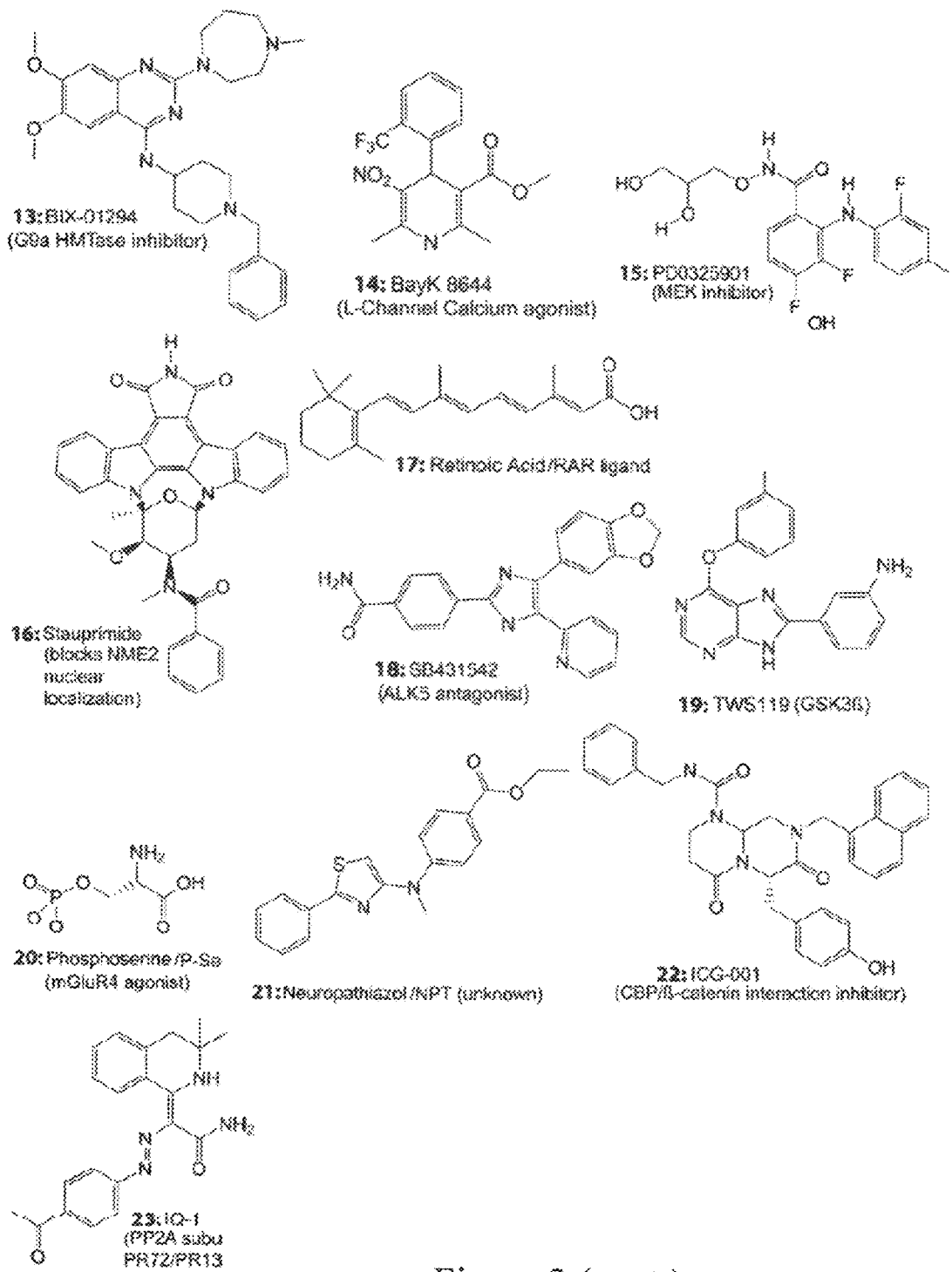

FIG. 3: Examples of stem cell regulators which can be used to activate the ADSC.

FIG. 4: Table demonstrating the light activation of ADSC. Five frequency ranges (2 in the green, 1 in the yellow an 2 in the red) where found to stimulate adipose-derived MSCs.

Figure 5:
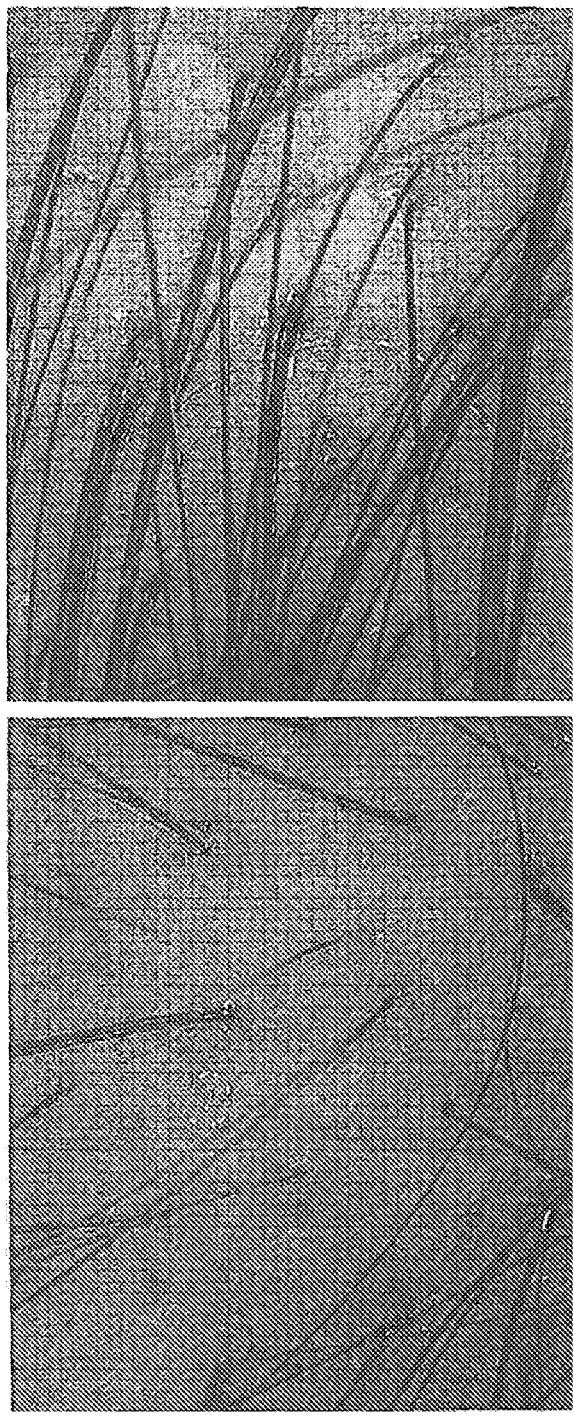
Figure 6:
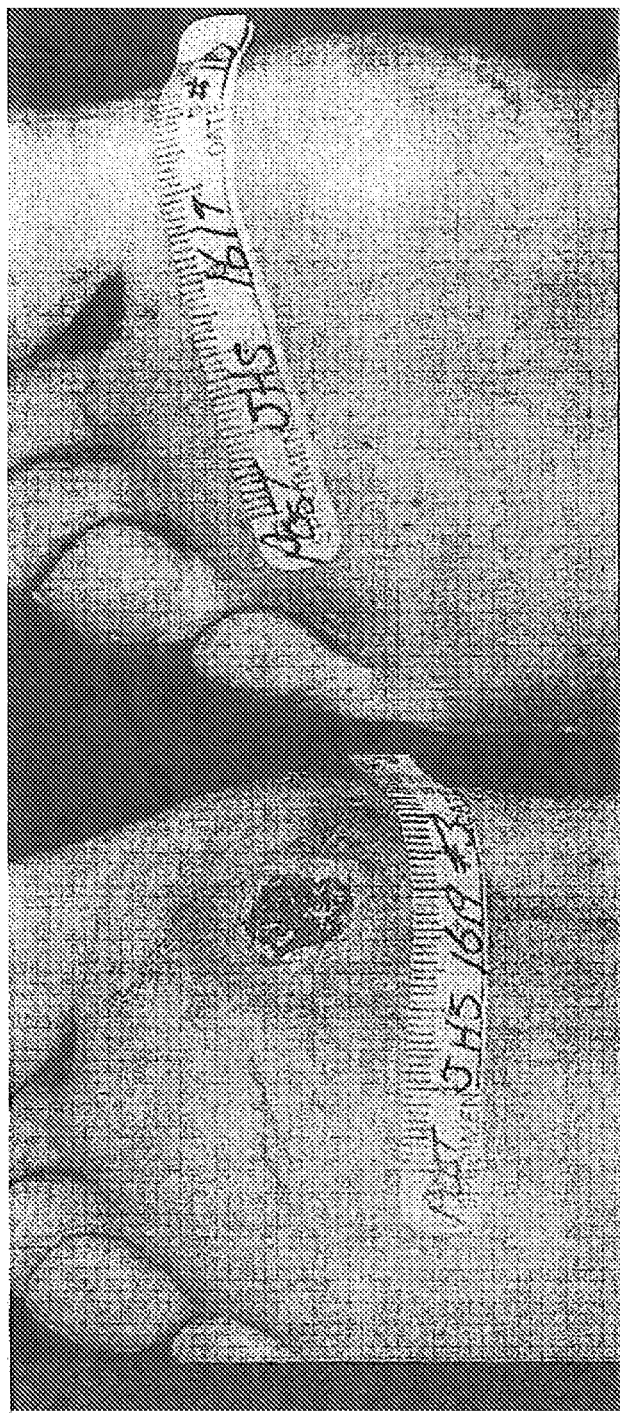
Figure 7:
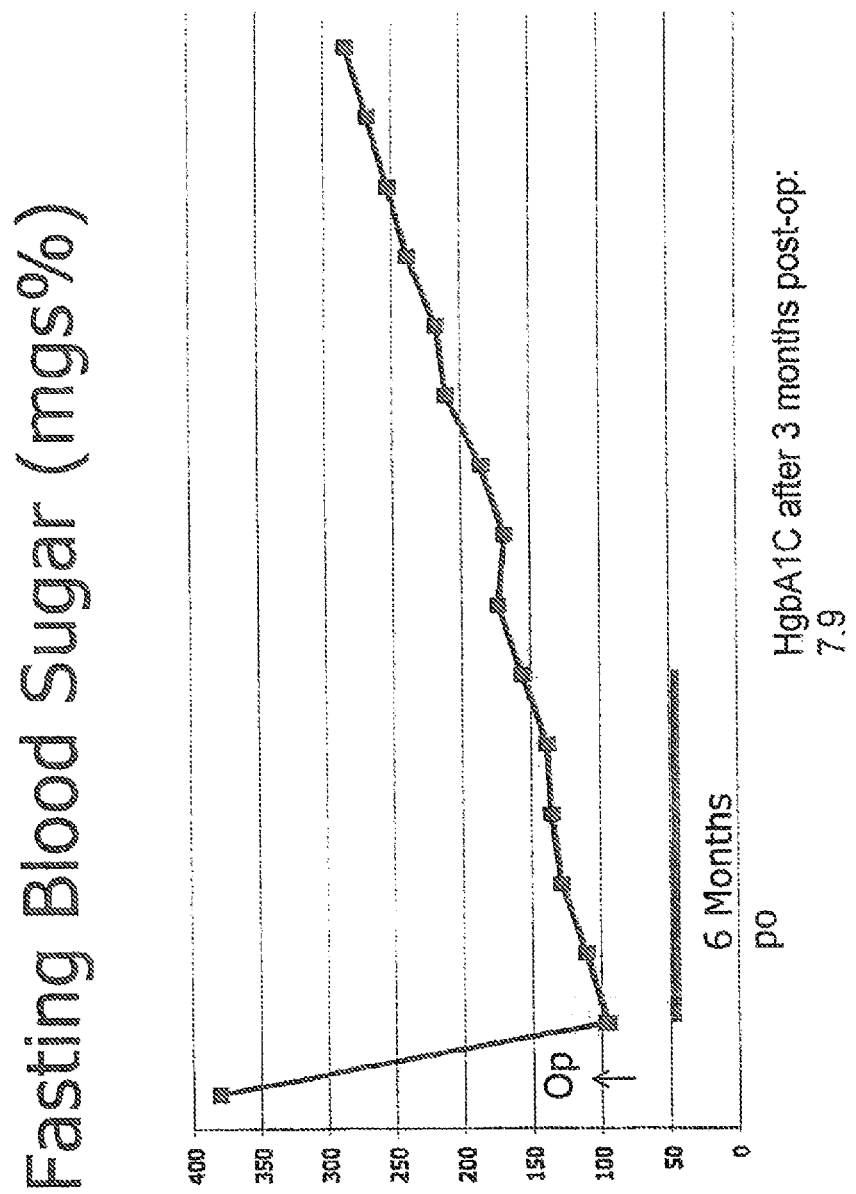

FIG. 5: Effect of intradermal injections of autologous adipose-derived stromal cells for cosmetic application in alopecia FIG. 6: Effect of intravenous administration of autologous adipose-derived stem cells on diabetic neuropathic ulcers FIG. 7: Case Study: Type II Diabetic. Intravenous treatment with activated autologous adipose-derived stem cells.

FIG. 8: Case Study: Type II Diabetic. Intravenous treatment with activated autologous adipose-derived stem cells.

Figure 9:
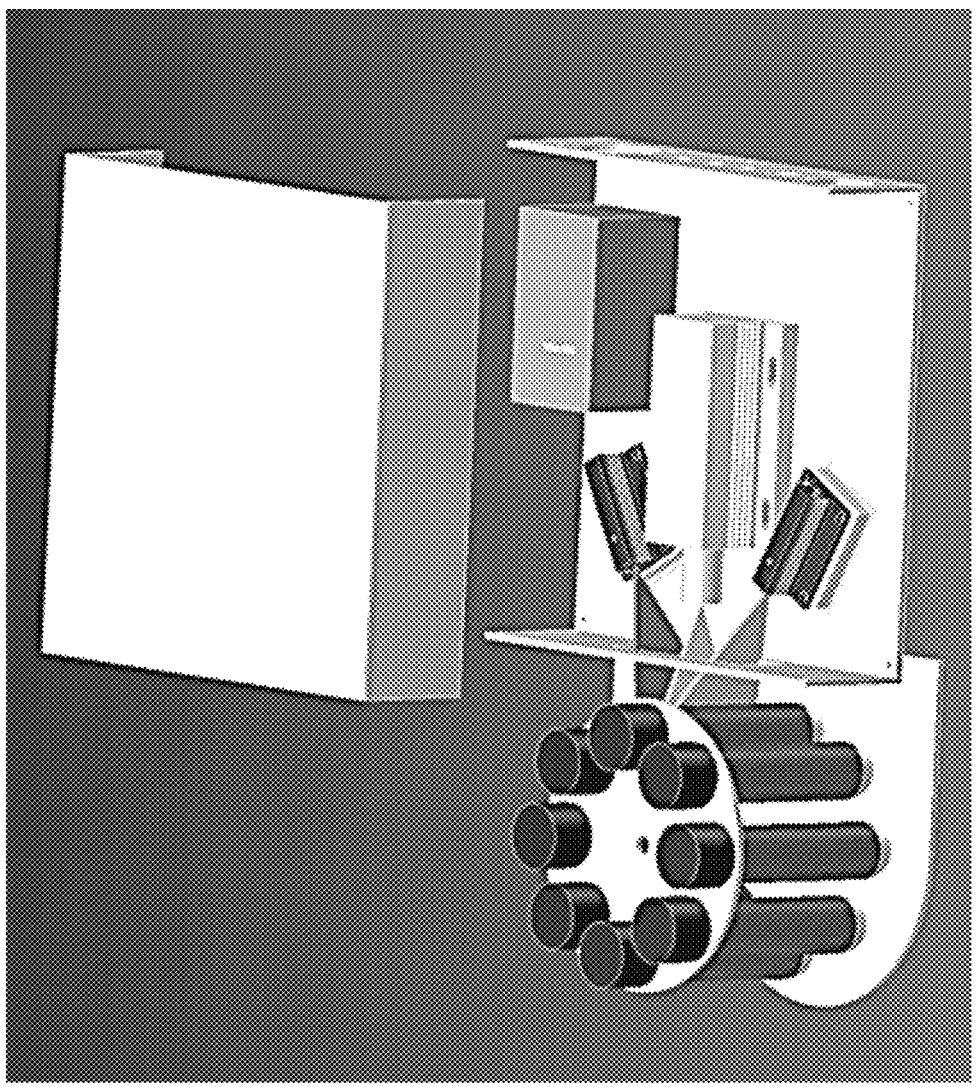

FIG. 9: Diagram of an apparatus for irradiating ADSC with one or more wavelengths of light.

EXAMPLE 1

Autologous Fat Transfer

Autologous fat transfer is a relatively common cosmetic and structural procedure involving the harvest of adipose tissue (fat) from one location and reimplantation in another location within the same individual (Coleman, S. R. (1995) Aesthetic Plast Surg 19(5): 421-5; Coleman, S. R. (2001) Clin Plast Surg 28(1): 111-9; Coleman, W. P., 3rd (1991) Plast Reconstr Surg 88(4): 736). However, as indicated above, this procedure is frequently compromised by inconsistent engraftment such that the implanted material is fully or partially resorbed or is replaced by scar tissue (Eremia, S. and N. Newman (2000), Dermatol Surg 26(12): 1150-8). At least part of the loss of function can be attributed to necrosis of implanted fat tissue during the time it takes for new blood vessels to form and feed the implant. Thus tissue implanted into highly vascular areas such as muscle beds shows better engraftment than when implanted into less well perfused tissues (Guerrerosantos, J., A. Gonzalez-Mendoza, et al. (1996) Aesthetic Plast Surg 20(5): 403-8).

Processed lipoaspirate prepared as described in this disclosure addresses this issue by supplementing the implant with additional endothelial precursors and stem cells. In a clinical application of this technology, processed lipoaspirate derived according to this disclosure is prepared and mixed with intact (non-disaggregated) adipose tissue fragments, as disclosed above. The composition comprising the mixture of adipose tissue and the activated stem cells may be implanted into the recipient to provide an autologous soft tissue filler for correction of contour defects (wrinkles, "divots," pockmarks, and larger deficits) (Coleman, S. R. (2001) supra) or for providing support to damaged structures such as the urethra (Palma, P. C., C. L. Riccetto, et al. (1997) J Endourol 11(1): 67-70; Lee, P. E., R. C. Kung, et al. (2001) J Urol 165(1): 153-8). It can also be use for breast and penile augmentation, as well as a filler in a breast that has had a cancer lumpectomy.

EXAMPLE 2

Type II Diabetes

A clinical trial on the intravenous administration of activated stem cells prepared as in embodiment above has been performed. The title of the trial was: Safety and efficacy of autologous adipose-derived stromal cells on Type II diabetes patients: 6 month post procedure results. Some data from the trial is shown in the accompanying figures. The abstract of the trial was:

"Stem cell therapies hold great promise for anti-aging benefits as they are regenerative in nature. Autologous adipose-derived stem cell transplants hold even more potential as they have no ethical barriers and require no out-of-surgery culture requirements. We have devised a procedure that entails the isolation of stromal cells from adipose-tissue derived from a mini-liposuction procedure, their activation from a quiescent stage to an active stage, and their reintroduction back into the patient via intravenous mode. This single procedure has now been performed on 176 subjects over a two and a half year period in four countries with no adverse effect. Because these were isolated case studies a formal clinical trial was then initiated to assess the safety and efficacy of the procedure on a controlled group of 34 patients with non-insulin and insulin-dependent type II diabetes mellitus with no cardiovascular or nephrological complications. After three months post-operation the patients showed a significant and sustained reduction in fasting glucose levels (from 9.64+3.88 mmol/l to 7.01+1.64 mmol/l; p=0.005 at 2 weeks to 7.71+2.29 mmol/l; p=0.01 at 12 weeks), glycosylated haemoglobin (from 9.11+2.06% to 7.73+1.19%; p=0.00001), C-peptide (from 2.75+1.02 to 2.27+1.45; p=0.045) and triglycerides (from 2.31+1.53 to 1.91+1.63; p=0.03). At six months post procedure nearly half the patients reverted back to pre-op conditions while the other half continues to see sustained decreases in diabetic parameters as compared to pre-op levels. Six month statistics showed Fasting blood sugar went from 9.64+3.88 mmol/l at pre-op to 8.50+2.86 mmol/l; p=ns at 24 weeks), glycosylated haemoglobin (from 9.11+2.06% to 8.10+1.82%; p=0.001), C-peptide (from 2.75+1.02 to 2.83+1.37;

p=ns) and triglycerides (from 2.31+1.53 to 2.01+1.35; p=ns). Most patients have noticed an increase in well-being parameters post-op. There was no significant change detected post-op in total cholesterols and other CBC, LFT and KFT values and no obvious adverse reaction has been noted. The results of the trial to date suggest that the autologous adipose derived stromal cell therapy appears to be safe and beneficial to type II diabetes patients by decreasing their resistance to insulin and decreasing diabetic cardiovascular risk factors. We believe that the stromal cell transplant is probably acting by increasing adiponectin levels in these subjects, an adipocytokine that is produced by adipose stromal cells and known to regulate insulin-resistance. Lifestyle and hypoglycemic medication changes also plays an important role in sustaining the effects observed." FIG. 3 shows statistical results.

EXAMPLE 3

Alopecia

Subcutaneous and intradermal administration of activated stem cells (prepared as in the described embodiment above) into the scalp of men with male pattern baldness has been performed. Increased follicle thickness, colouration, and new hair follicle growth has been observed in a number of cases. No adverse reaction has yet to be noticed. An illustrative example of this is provided in the accompanying figures.

EXAMPLE 4

99Tc HMPAO labelling of adipose derived stromal vascular fraction cells.
You will need the following:
1) hexamethylpropylene amine oxime (HMPAO) vials from Ceretec.
2) Tc99m (370 MBq)
3) sterile 15% NaCl solution
4) sterile Saline
5) 2 ml sterile centrifuge (eppendorf) tubes
6) 15 ml sterile plastic tubes screw-top.
1. Take 10% of the stromal vascular fraction to be injected.
2. Spin the sample at 600×g for 5 min. Remove the supernatant.
3. For lysis of re blood cells add 10 ml hypertonic saline—NaCl 1.8% (8.8 ml saline+1.2 ml NaCl 15%)
4. Let sit for 30 sec.
5. Spin at 600×g for 5 min and remove supernatant.
6. Reconstitute pellet with 0.5 ml Saline.
7. Add to the Ceretec tube 1.5 ml saline and vortex 5-6 times.
8. Take 0.5 ml of Ceretec and add 370 MBq Tc99m. Vortex 5-6 with over a 30 min period.
9. Ad this mixture to the reconstituted stromal vascular fraction cells. Let this sit for 15 min, with gentle shaking every 2-3 min
10. Spin the mixture at 600×g for 5 min. Wash with saline an re-spin at 600×g for 5 min. Repeat once more. Reconstitute cells in 2 ml saline.
11. With a two ml syringe inject the cells by i.v. with a 1-2 min period.
12. Observe the patient in case of allergic symptoms.
13. Do a full body gamma scan on patient 12-24 hrs later.
Any feature or combination of features described herein are included within the scope of the present invention provided that the features included in any such combination are not mutually inconsistent as will be apparent from the context, this specification, and the knowledge of one of ordinary skill in the art. For purposes of summarizing the present invention, certain aspects, advantages and novel features of the present invention have been described herein. Of course, it is to be understood that not necessarily all such aspects, advantages or features will be embodied in any particular embodiment of the present invention. Additional advantages and aspects of the present invention are apparent in the following detailed description and claims.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

A number of publications and patents have been cited hereinabove. Each of the cited publications and patents are hereby incorporated by reference in their entireties.

The invention claimed is:

1. A method of preparing a population of adipose-derived stem cells (ADSC) for autologous implantation to a subject, comprising:
(i) collecting adipose tissue and blood from a subject,
(ii) isolating ADSCs cells from the adipose tissue and platelet rich plasma (PRP) from the blood,
(iii) activating the isolated ADSCs by irradiation with yellow light at a wavelength of 575-595 nm and at 5-20 mW, red light at wavelength of 630-635 nm and at 10-100 mW, and green light at a wavelength of 510-540 nm and at 10-60 mW, for 30-60 minutes,
(iv) mixing the activated ADSCs with the PRP, thereby preparing a population of ADSCs for autologous implantation.

2. The method of claim 1, wherein the ADSCs are irradiated with yellow light at a wavelength of 595 nm and at 20 mW, red light at wavelength of 635 nm and at 60 mW, and green light at a wavelength of 535 nm and at 60 mW, for 30-60 minutes.

3. The method of claim 1, wherein the isolated ADSCs in step (ii) are exposed to one or more growth factors.

4. The method of claim 3 wherein the growth factors are Epidermal Growth Factor (EGF); Platelet-Derived Growth Factor (PDGF); Fibroblast Growth Factor (FGF); Transforming Growth Factor-β (TGF-β); Erythropoietin (EPO); Insulin-like Growth Factor-I (IGF-I); Insulin-like Growth Factor-II; and/or Tumor Necrosis Factor-α (TNF-α).

5. The method of claim 3 wherein the PRP comprises one or more growth factors.

6. The method of claim 1, wherein step (i) comprises exposing the adipose tissue to a lipid dissolving agent.

7. The method of claim 6 wherein said lipid dissolving agent is lecithin.

8. The method of claim 1, wherein step (i) comprises exposing the adipose tissue to collagenase.

9. The method of claim 1, wherein the adipose tissue is isolated from the subject by liposuction and/or lipoplasty.

10. The method of claim 1 comprising:
i) processing the sample of adipose tissue from the subject to obtain a concentrated population of ADSC, said processing comprising: removing free lipid and single cell components of the tissue by rinsing; disaggregating the tissue using mechanical forces, collagenase and lecithin digestion, separating and concentrating the ADSC using centrifugation; and ii) activating the population of ADSC by irradiating the cells with yellow light at a wavelength of 575-595 nm and at 5-20 mW, red light at wavelength of 630-635 nm and at 10-100 mW, and green light at a wavelength of 510-540 nm and at 10-60 mW, for 30-60 mins, and incubating the ADSCs in the presence of PRP prepared from the patient to be treated at 30° C. to 38° C. for 5-120 minutes.

* * * * *